United States Patent [19]

Klose et al.

[11] 4,432,674

[45] Feb. 21, 1984

[54] METHOD AND DEVICE FOR ANALYZING THE SOLID MATTER CONTENT IN A HYDRAULIC CONVEYING STREAM OF A CARRIER LIQUID WITH SOLID PARTICLES

[75] Inventors: Reinhard Klose; Günter Glienke, both of Salzgitter, Fed. Rep. of Germany

[73] Assignee: Stahlwerke Peine-Salzgitter AG, Fed. Rep. of Germany

[21] Appl. No.: 405,410

[22] Filed: Aug. 5, 1982

Related U.S. Application Data

[63] Continuation-in-part of Ser. No. 171,017, Jul. 18, 1980, abandoned.

[30] Foreign Application Priority Data

Jul. 20, 1979 [DE] Fed. Rep. of Germany ....... 2929430

[51] Int. Cl.³ ............................................. B65G 53/66
[52] U.S. Cl. .................................. 406/19; 73/863.23; 73/863.54
[58] Field of Search ...................... 406/1, 2, 12, 19, 31, 406/197, 198; 73/863.54, 863.23, 61 R, 61.4

[56] References Cited

U.S. PATENT DOCUMENTS

| | | | |
|---|---|---|---|
| 3,514,217 | 5/1970 | Reiss | 406/19 |
| 3,517,969 | 6/1970 | Wicks III | 406/197 |
| 3,747,411 | 7/1973 | McDermott et al. | 73/863.54 |

Primary Examiner—Jeffery V. Nase
Attorney, Agent, or Firm—McGlew and Tuttle

[57] ABSTRACT

A method and apparatus for analyzing the solid matter content of a hydraulically conveyed stream in a conveyor pipeline to be monitored and controlled, comprising, taking of a representative sample of the material in the pipeline across the diameter of the pipeline, separating the solid matter particles in the sample and increasing the liquid proportion in the sample, depositing the separated particles on a filter surface, analyzing the distribution of size and shape of the particles on the filter and adjusting the conveyor accordingly to control a feed pressure in the pipeline and a liquid content of material in the pipeline. The analyzing step is performed by a microscope and a television camera which converts an optical image from the microscope into a signal readable by a computer which, in turn, through a microprocessor, controls a feed pump and liquid input valve.

10 Claims, 2 Drawing Figures

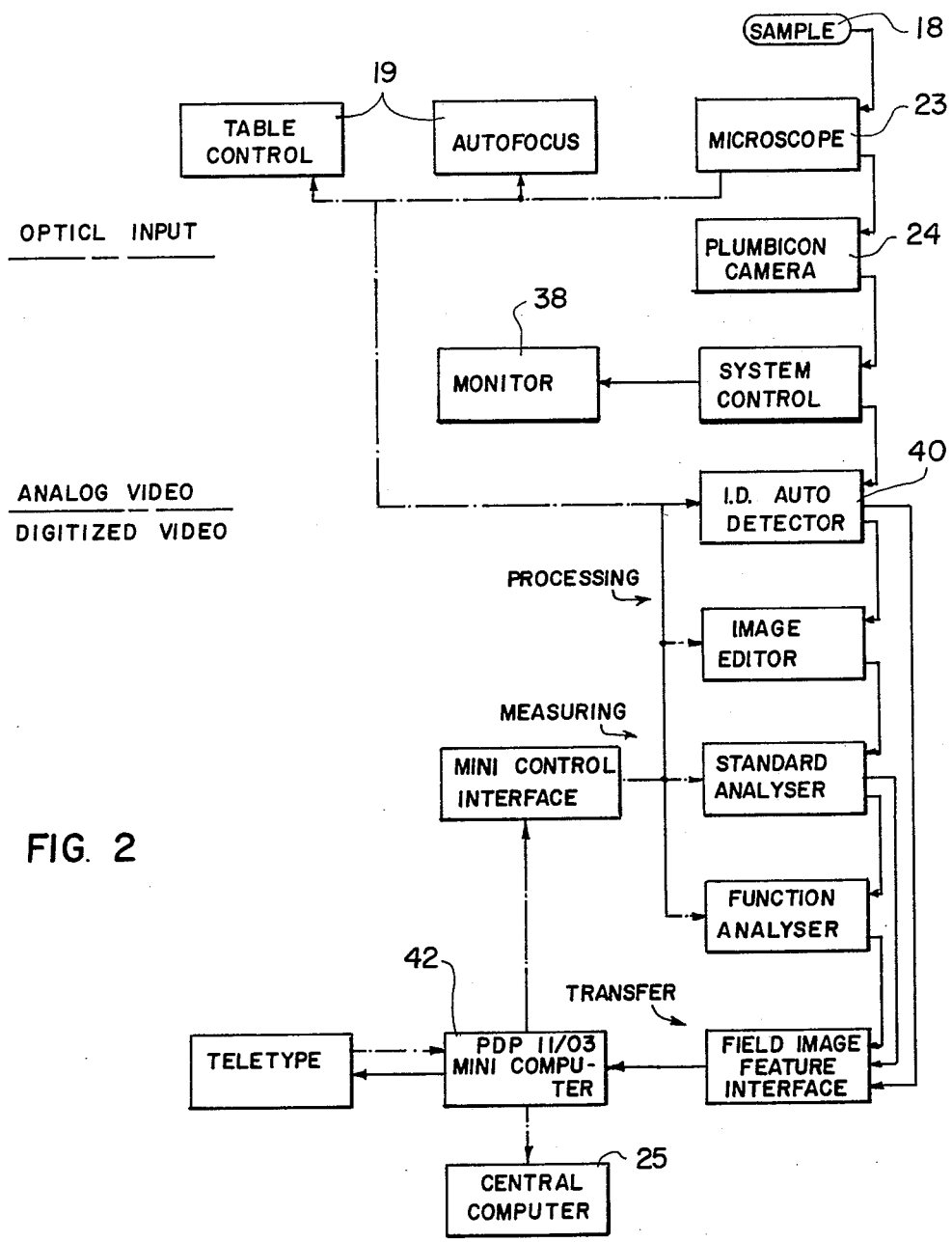

METHOD AND DEVICE FOR ANALYZING THE SOLID MATTER CONTENT IN A HYDRAULIC CONVEYING STREAM OF A CARRIER LIQUID WITH SOLID PARTICLES

CROSS-REFERENCE TO RELATED APPLICATIONS

The present application is a continuation in part of Ser. No. 171,017 filed July 18, 1980 and now abandoned.

FIELD AND BACKGROUND OF THE INVENTION

The present invention relates to bulk material conveyors in general and, in particular, to a new and useful method of analyzing the solid matter content of a hydraulic conveying stream to be monitored and controlled, which contains a carrier liquid and solid particles, and to a device for carrying out the method.

In the hydraulic transportation of mineral material, such as coal, ore, etc., it is well known that the proportion of solid matter to carrier liquid is of fundamental importance for maintaining a continuous conveying stream. German Auslegungschrift No. 2,557, 872, which is here incorporated by reference for background information, for example, discloses a method according to which the solid matter to be conveyed, after being broken up into fragments of a suitable size is combined with a stream of carrier liquid to obtain a two-phase pumpable slurry. That is, a slurry with a liquid part and a particle part is obtained. The objective of this prior art method is to obtain a substantially constant weight rate of flow of the slurry through the pipeline and to automatically control the solid matter concentration in the slurry to keep it at a substantially constant value.

Experience has shown that the prior art methods and arrangements are not satisfactory for maintaining an undisturbed continuous material flow in the pipeline. The present invention is based on the observation and experience that, despite careful monitoring and control of the proportions of solid matter and carrier liquid, a trouble-free hydraulic transportation of minerals in pipelines cannot be insured because, along extended conveying sections, the flow conditions continue to vary even if the solid matter-to-carrier liquid proportion remains constant.

This condition is apparently caused by a continual frictional contact of the solid particles with each other and with the pipe walls, resulting in a varying particle size distribution within the entire solid matter proportion. This variation of the particle size distribution necessarily changes the consistency and, thus, the flow conditions of the slurry to be conveyed so that, for example, due to an increase in the critical speed of conveyance and to deposits in the line, a continuous flow is no longer insured.

SUMMARY OF THE INVENTION

The present invention is directed to a method and device for improving the solid matter flow in the carrier liquid, as compared with the prior art, and for permitting a rapid deterioration of the consistency of the slurry at each instance, in order to precisely monitor and control the conveyed stream.

It has been found that it is necessary to ascertain the particle size distribution, that is, the proportion of coarse, medium sized and fine fractions, exactly and expeditiously, to determine therefrom and control the feed pressure for an undisturbed continuous transportation.

To this end, in accordance with the present invention, a method is provided having the following inventive features and steps:

(a) the taking of a representative sample from the cross-section of flow in a pipeline;

(b) the separation of the same particles from each other, while increasing the liquid proportion, if necessary;

(c) depositing the thus separated samples on a filter surface;

(d) analyzing the solid particles as to shape and size; and (e) adjusting the amount and/or feed pressure of the carrier liquid in accordance with the result of the analysis.

The representative sample is advantageously taken from a vertically extending section of the pipeline, by means of a sampling tube which is movable perpendicularly to the flow direction along the entire inside diameter of the line.

The sample is taken in a vertical pipeline section because it may be assumed that no significant velocity and concentration distributions occur at such a location.

The sample is then diluted, preferably with an alcohol/glycerol mixture, to a very low concentration so that the particles are separated from each other. This insures that no agglomerations remain. The sample processed in this way is introduced into a pressure diaphragm filtering device and filtered under pressure through a diaphragm filter having a pore size 0.0008 mm. The particles are individually held back on the filter surface and can then be analyzed. For this purpose, the specimen is stretched in clamps to ensure it remains in a plane, since the drying sets in during the analysis.

The analysis is advantageously made with the aid of a picture analyzing system. To analyze the picture, an optical signal (from a microscope) is converted to an electrical signal (from a television camera) and further to a digital signal (from a computer). All data specific to the particles are determined, such as, perimeter, area, length, width, etc. The entire filter surface is examined, so that any particle within the range of 0.001 to 3 mm in diameter is investigated. This is obtained by means of several magnifying objectives which overlap in certain zones and are put into operation successively and automatically to effect the analysis. The entire operation is computer controlled and, inclusive of the sampling and preparation, takes less than one hour, so that the necessary pressure control and the manual or automatic adjustment, which is known per se, of the solid matter to liquid proportion in the conveying pipe system can follow. While those skilled in the field of automatic and computer assisted analysis, particularly image analysis, will be able to practice this invention without undue experimentation, it is noted that the invention can also be practiced without recourse to computers or image analysis but manually. This method is of course slower, however.

Details explaining automatic computerized image analysis can be found in the published works to be cited later.

To increase the liquid proportion to an extent needed for the analysis, water, gasoline, alcohol, glycerol, rosin, or combinations of these substances may be used, for example.

It has proven to be particularly advantageous to provide an analysis of the particle size range of approximately 0.001 mm to 3 mm and to use a plurality of objectives, with each of the objectives covering definite particle size ranges and the objectives overlapping each other.

Another object of the present invention, therefore, is to provide a device for analyzing a solid matter content of a carrier liquid and solid particle mixture in a pipeline of a conveyor system and controlling at least one of a pressure and liquid proportion in the pipeline of the conveyor system, comprising, sample extraction means for removing a sample of the mixture across a diameter of the pipeline, dilution means connected to the sample extraction means for receiving the sample and diluting it to disperse the particles therein, filter means connected to the dilution means for spreading the dispersed particles of the sample on a filter, analyzing means associated with the filter for scanning the filter and evaluating the distribution and size of the particles on the filter, and control means connected to the analyzing means and the conveyor systems for regulating at least one of the feed pressure and liquid proportion in the pipeline according to the evaluated distribution and size of the particles.

Further objects of the present invention are to provide a method of analyzing the solid matter in a pipeline which is simple and effective in controlling the pressure and/or liquid proportion of the material in the pipeline and to provide a device for achieving the method which is simple in design, rugged in construction and economical to manufacture.

The various features of novelty which characterize the invention are pointed out with particularity in the claims annexed to and forming a part of this disclosure. For an understanding of the invention, its operating advantages and specific objects attained by its uses, reference is made to the accompanying drawing and descriptive matter in which a preferred embodiment of the invention is illustrated.

BRIEF DESCRIPTION OF THE DRAWINGS

In the Drawings:

FIG. 2 is a flow chart showing the automatic image analysis of the invention.

DETAILED DESCRIPTION OF THE PREFERRED EMBODIMENT

Figure 1:
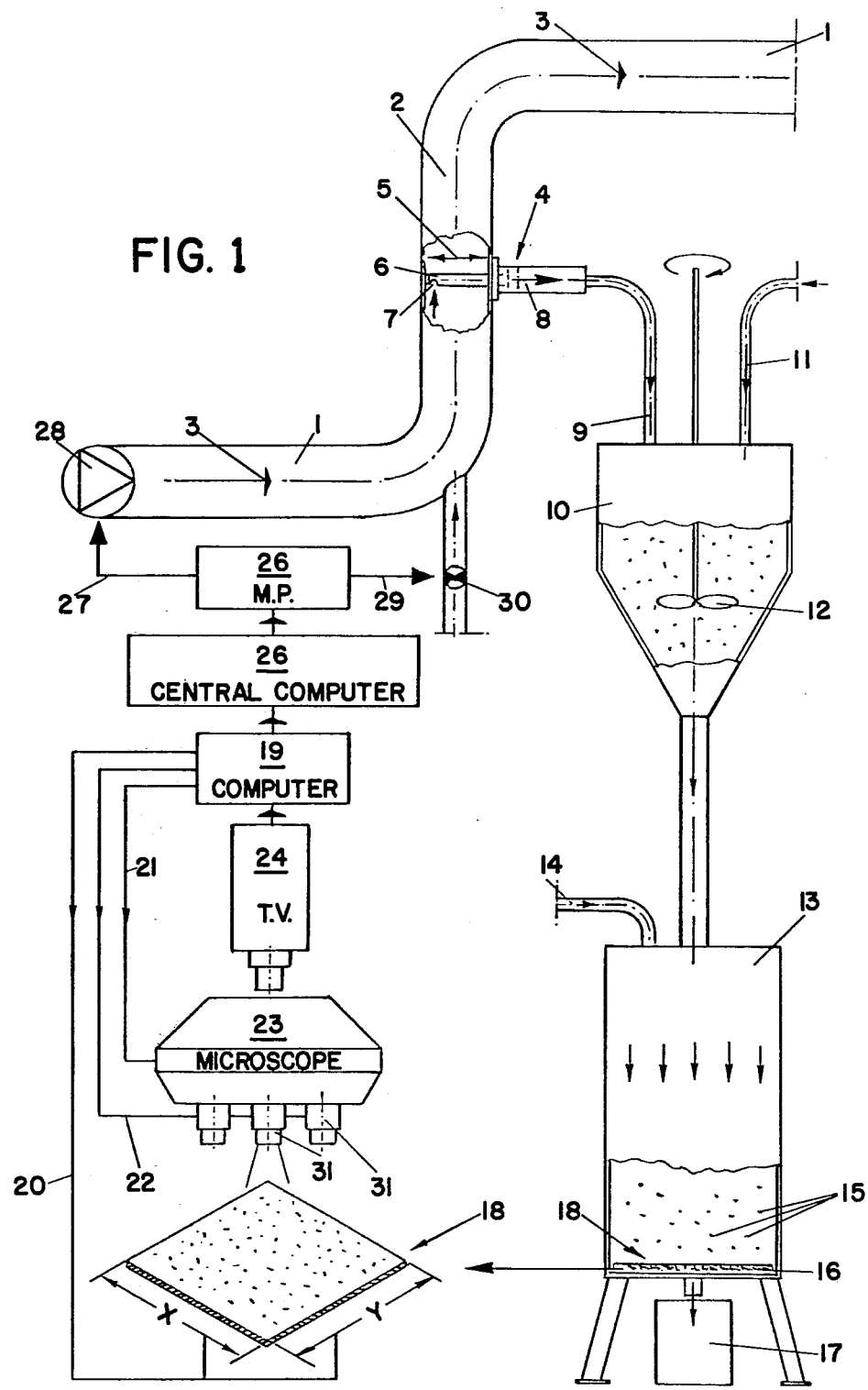
FIG. 1 is a schematic diagram of the system according to the inventive method and apparatus.

In the following description, the invention is explained in more detail while referring to the accompanying drawings.

In FIG. 1 and at a vertical section 2 of a conveying pipeline system 1, a sampling device 4 is provided, comprising a sampling tube 6 which is movable perpendicularly to the flow direction 3, along the inside diameter 5 of the pipeline. Sample tube 6 is provided at its free end with an inlet aperture 7 facing upstream against the flow direction 3. Sampling tube 6 is moved along inside of diameter 5 by means of drive mechanisms known per se, for example, a piston-cylinder-unit 8, which may be actuated either pneumatically or hydraulically.

The sample taken by sampling tube 6 is directed into a collecting vessel 10 through a sample line 9, as indicated by the arrows. The sample is mixed in collecting vessel 10 with a particle separating substance or diluent, such as water, gasoline, alcohol, glycerol, rosin or a combination of these substances, which are supplied to vessel 10 through another line 11. The sample is dispersed in the supplied diluent by means of a stirrer 12, and the particles, in a separated stage, are conducted into a filter container 13. For filtering, a pressure diaphragm filter is provided, and a particle-free gas, for example nitrogen, is supplied into container 13 through a line 14.

The solid particles 15 deposit on the surface of filter 16, while the liquid components are drained into a vessel 17. These measures ensure that the particles become deposited on the surface of the filter 16 individually, without being agglomerated or overlapping each other, and that the sample can be analyzed reliably. The specimen 18 is then stretched or laid on a table (not shown) which is movable in two horizontal directions, x and y. The specimen table is controlled by a computer 19 through a line 20 so that all parts of the specimen 18 are scanned. The computer 19 also controls, through a line 21, the automatic change and, through a line 22, controls the automatic focussing of objectives 31 of a microscope 23.

In order to effect the picture analysis, the optical signal of microscope 23 is converted by means of a television camera 24 into an electrical signal, and by means of the computer into a digital signal. The result of the above-described analysis is transmitted by computer 19 to a central computer 25 from which, after an evaluation of the analysis, corresponding control pulses are delivered to a microprocessor 26 for controlling the conveying stream in pipeline 1, i.e. to effect a variation of the speed of a feed pump 28 through a line 27, and/or to actuate a valve 30 through a line 29, in order to add water or other liquid carriers and thus to increase the liquid proportion in pipeline 1.

Such a device makes it possible to monitor and effect the necessary control of the pressure and the component proportion in a conveying pipeline system automatically and within a short period of time to obtain an undisturbed, continuous flow.

The analysis technique is shown in greater detail in FIG. 2. An image produced with the assistance of the light-optical microscope 23, is transformed by the television camera 24 into an electrically analogous image. For manual analysis, the image can be provided to a T.V. monitor 38. The electrically analogous image is transformed into an electrically digital image via a detector 40. This digital image can be analyzed according to certain criteria by various known modules. Measurement values are transferred by an interface to the central or systems computer 25 where they are evaluated, stored and as a rule made available to an operator by means of a printer. The measuring principle is based on the contrast between the object which is to be measured, and its surroundings. The greater the contrast, or as an image analyst would say, the greater the grey shade difference between object and surroundings, the more defined is the image. The optical equipment and the number of lines provided by the video system are the major factors as regards particle size analysis. A system's ability to measure the distribution range depends upon the optics used and on the sample quantity. The time required to complete an analysis depends, amongst other things, on whether an image analysis system is used which relies more on software or more on hardware.

A Zeiss Universal light-optical microscope 23 is used for the optical input. The analysis is carried out with the assistance of two long-distance lenses 31 which are capable of enlarging by 4 and 40 times respectively. Two enlargements are required since, according to the laws of optics, one enlargement cannot cover the range of 1 micron to 3 mm. The lens is changed automatically via an electric motor installed at the revolving lens turret. The x-y scanning table (object slide) has a working area of 100 mm in each direction with a reproducibility of ±5 microns.

The automatic focus is so programmed that the focussing time is kept to a minimum.

Lens change, scanning table and automatic focus are controlled and monitored by the computer 19 of the image analysis system.

The smallest element used in transforming the optical image into an electrically analogous image is the so-called picture point. Its absolute size is a measure of the system's acuity. An image or area of measurement of the above mentioned system is composed of approximately 700,000 picture points. It requires 4–5 picture points (in this case 0.45 microns) in order to measure an object with precision.

The ID detector 40 uses the differences in contrast, i.e. the grey shade difference, between the particles and the background, and transforms the analogous into a digital image. The further processing takes place in the hardware modules, such as in the function analysis. It can thus be determined which measuring process should be carried out on each particle (perimeter, area, Feret's diameter, etc.). The subsequent evaluation of the measurements takes place in an in-process computer 42 which forms part of the system.

The sample 18 under the microscope 23 is first of all scanned by the ×40 lens in a meandering fashion in order to measure the finest particles of 1 to 50 microns. The screened area is an octagon inscribed into a circular when the specimen 18 is circular instead of square as shown in FIG. 1. The number of measured fields depends upon the particle size distribution. The measurement fields are statistically spread over the entire specimen. Focussing takes place for each field. Each particle is measured according to the 4 Feret diameters under 0°, 45°, 90° and 135°. When the finest particles have been measured, the lens is automatically changed to the ×4 enlargement and starts with the first measurement field. With this smaller enlargement, the entire specimen is measured, i.e. the lens is placed over each measurement field in turn. This means that 98 cm² of the filter surface can be covered. This measurement also determines and records the above mentioned 4 Feret diameters of each particle.

The area covered by the ×4 enlarger lies between 20 microns and 3150 microns. One picture point on this scale of enlargement represents 4.6 microns, while with an enlargement of 40 times, one picture point equals 0.45 microns. There is an overlap area of the two lenses between 20 microns and 50 microns. By suitable selection of adjustment, it can be ascertained during the subsequent evaluation, that there is a resulting constant distribution function. Once the entire specimen has been measured, there then follows the evaluation and transfer of the results to the computer 25.

For additional information which is available to those skilled in the art concerning the use of computers, video systems and optical microscopes for image analysis can be found in

[1] Photomikroskop Ultraphot: Auflichtbeleuchtung Carl Zeiss, Oberkochen
[2] W. Cebulla "Quaubitalive Mikroskopie", Carl Zeiss, Oberkochen
[3] F. K. Möllring "Mikroskopieren von Amfangan" Carl Zeiss, Oberkochen
[4] "RT-11 System User's Guide" 1978 Digital Equipment Co.
[5] "Quantimet System 23" Cambridge Analysing, Instruments Ltd.

What is claimed is:

1. A method of analyzing the solid matter content of a hydraulically conveyed stream in a conveyor pipeline to be monitored and controlled, which stream contains a carrier liquid and solid particles, comprising:
   (a) taking a representative sample from the entire diameter of the conveyor pipeline;
   (b) separating the sample particles from each other, while increasing the liquid proportion in the sample;
   (c) depositing the thus separated sample on a filter surface;
   (d) analyzing the solid particles as to shape and size; and
   (e) adjusting at least one of the amount of the carrier liquid and a feed pressure in the pipeline according to the result of the analysis.

2. A method, as claimed in claim 1, wherein, to increase the liquid proportion, at least one of water, gasoline, alcohol, glycerol and rosin is used.

3. A method, as claimed in claim 1, wherein a granulometric analysis is made for step (d) which covers the size range from 0.001 mm to 3 mm and wherein an entire particle size distribution on the filter surface is determined by a plurality of overlapping objectives for different particle size ranges.

4. A method, as claimed in claim 1, wherein the representative sample is taken from a vertically extending pipeline section.

5. A method, as claimed in claim 1, wherein the analyzing is accomplished by optically scanning the filter surface.

6. A device for analyzing a solid matter content of a carrier liquid and solid particle mixture in a pipeline of a conveyor system and controlling at least one of a feed pressure and liquid proportion in the pipeline of the conveyor system, comprising: sample extraction means for removing a sample of the mixture across a diameter of the pipeline; dilution means connected to said sample extraction means for receiving the sample and diluting it to disperse the solid particles therein; filter means connected to said dilution means for spreading the dispersed solid particles of the sample on the filter means; analyzing means associated with said filter means for scanning the filter means and evaluating the distribution and size of the solid particles on the filter means; and control means connected to said analyzing means and to the conveyor system for regulating at least one of the feed pressure and liquid proportion in the pipeline according to the evaluation of the distribution and size of the solid particles on the filter means.

7. A device, as claimed in claim 6, wherein said sample extraction means comprises a sample tube having an open end facing upstream of a flow of the carrier liquid and solid particle mixture, and an actuator connected to said sample tube for moving said open end across the diameter of said pipeline.

8. A device, as claimed in claim 6, wherein said dilution means comprises a collecting vessel for receiving the sample and for receiving a diluent, and a stirrer movable in said collecting vessel for stirring and combining the sample with the diluent.

9. A device, as claimed in claim 6, wherein said filter means comprises a container for receiving the sample with dispersed solid particles therein and for receiving a pressure filtering medium for moving the sample against said filter means to disperse the solid particles on said filter means.

10. A device, as claimed in claim 6, wherein said analyzing means comprises a microscope having a plurality of objectives, each adapted for scanning a selected size of distributed solid particles on the filter, a television camera for converting an optical image from said microscope into an electronic signal, a computer connected to said television camera for converting said electronic signal into a digital signal and for moving said filter means to establish scanning by said microscope, a feed pump and liquid inlet valve connected to said pipeline and microprocessor connected to said pump and valve and to said computer for regulating said pump and valve according to said digital signal.

* * * * *